United States Patent [19]

Cieslak et al.

[11] 4,334,519
[45] Jun. 15, 1982

[54] PORTABLE HEATER FOR GENERATING AND CIRCULATING HEAT IN WEARING APPAREL

[76] Inventors: Stanley Cieslak, 14 Creek Rd.; Leonard K. Cieslak, 15 Creek Rd., both of McKees Rocks, Pa. 15136

[21] Appl. No.: 186,954

[22] Filed: Sep. 15, 1980

Related U.S. Application Data

[63] Continuation-in-part of Ser. No. 49,059, Jun. 18, 1979, Pat. No. 4,281,418, which is a continuation-in-part of Ser. No. 875,815, Feb. 7, 1978, Pat. No. 4,180,922.

[51] Int. Cl.³ .................................................. A61F 7/08
[52] U.S. Cl. ..................... 126/204; 126/263; 128/382; 128/399
[58] Field of Search ............... 126/204, 263; 2/160, 2/69, 211; 36/216; 165/46; 128/382, 399, 402, 403

[56] References Cited

U.S. PATENT DOCUMENTS

| | | |
|---|---|---|
| 518,579 | 4/1894 | Annenberg et al. |
| 912,527 | 2/1909 | Batter . |
| 1,199,914 | 10/1916 | Mossor . |
| 2,648,325 | 8/1953 | Siple ............................. 128/402 X |
| 3,000,616 | 9/1961 | Spangler ............................ 36/2.6 |
| 3,670,716 | 6/1972 | Esposito ............................ 126/204 |
| 3,688,762 | 9/1972 | Chi et al. ......................... 126/204 |
| 3,737,620 | 6/1973 | Harvey . |
| 3,744,053 | 7/1973 | Parker et al. ..................... 165/46 X |
| 3,884,216 | 5/1975 | McCartney ........................ 126/204 |
| 3,906,926 | 9/1975 | Staples ............................. 126/263 |
| 3,951,127 | 4/1976 | Watson et al. ................. 126/263 X |

FOREIGN PATENT DOCUMENTS 936887 7/1949 Fed. Rep. of Germany ...... 126/263

Primary Examiner—Samuel Scott
Assistant Examiner—Randall L. Green
Attorney, Agent, or Firm—Carothers and Carothers

[57] ABSTRACT

A portable heater for generating and circulating heat in wearing apparel. The heater consists of a compact insulated case having a cavity therein which is adapted to receive a chemical heat cartridge which gives off heat through an exothermic chemical reaction when an activator or catalyst is added to the chemical content of the cartridge. A liquid reservoir is positioned in the case for radiant heat transfer from the chemical heat cartridge. A flexible liquid conduit has opposite ends thereof connected for circulation of the heated liquid from the reservoir in a closed circuit, and a pump is provided for circulating the heated liquid through the conduit on demand.

3 Claims, 6 Drawing Figures

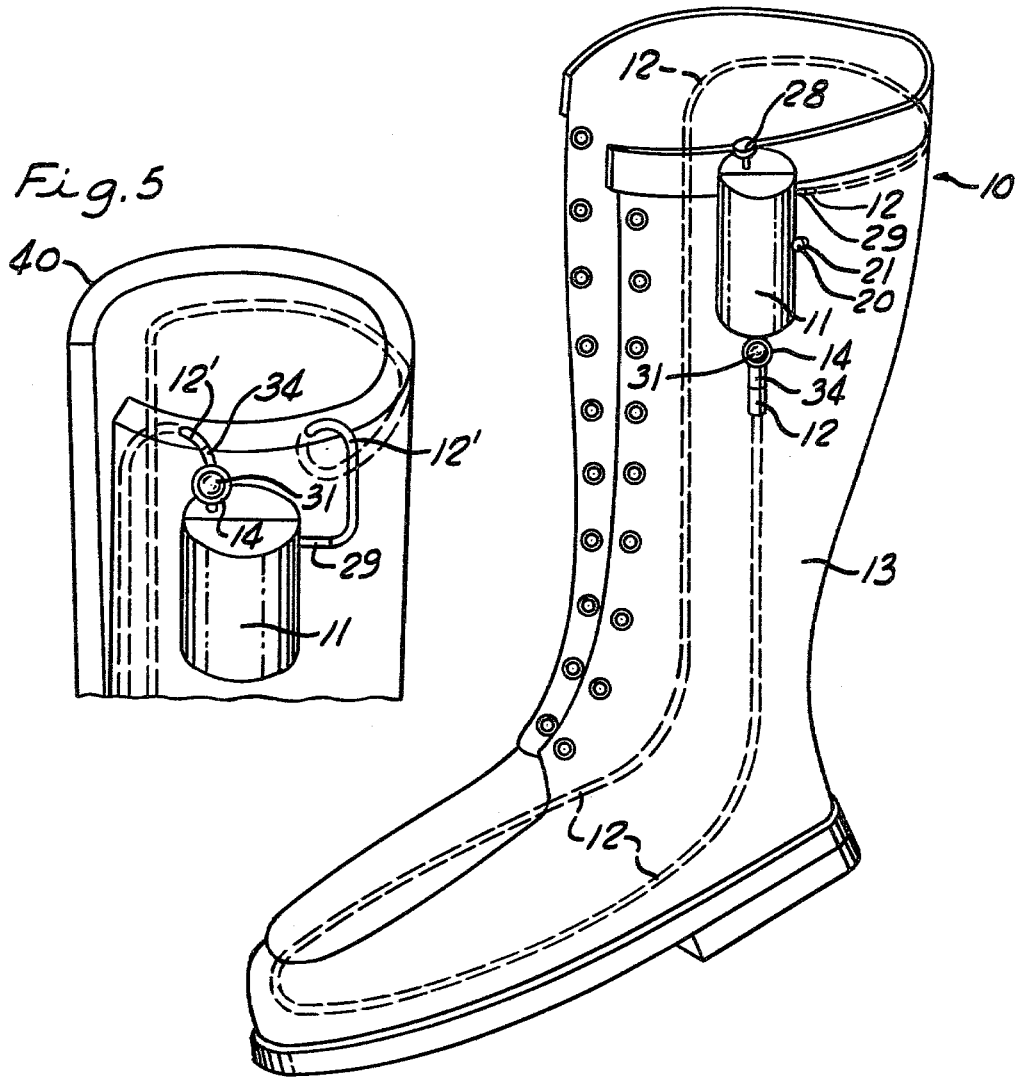

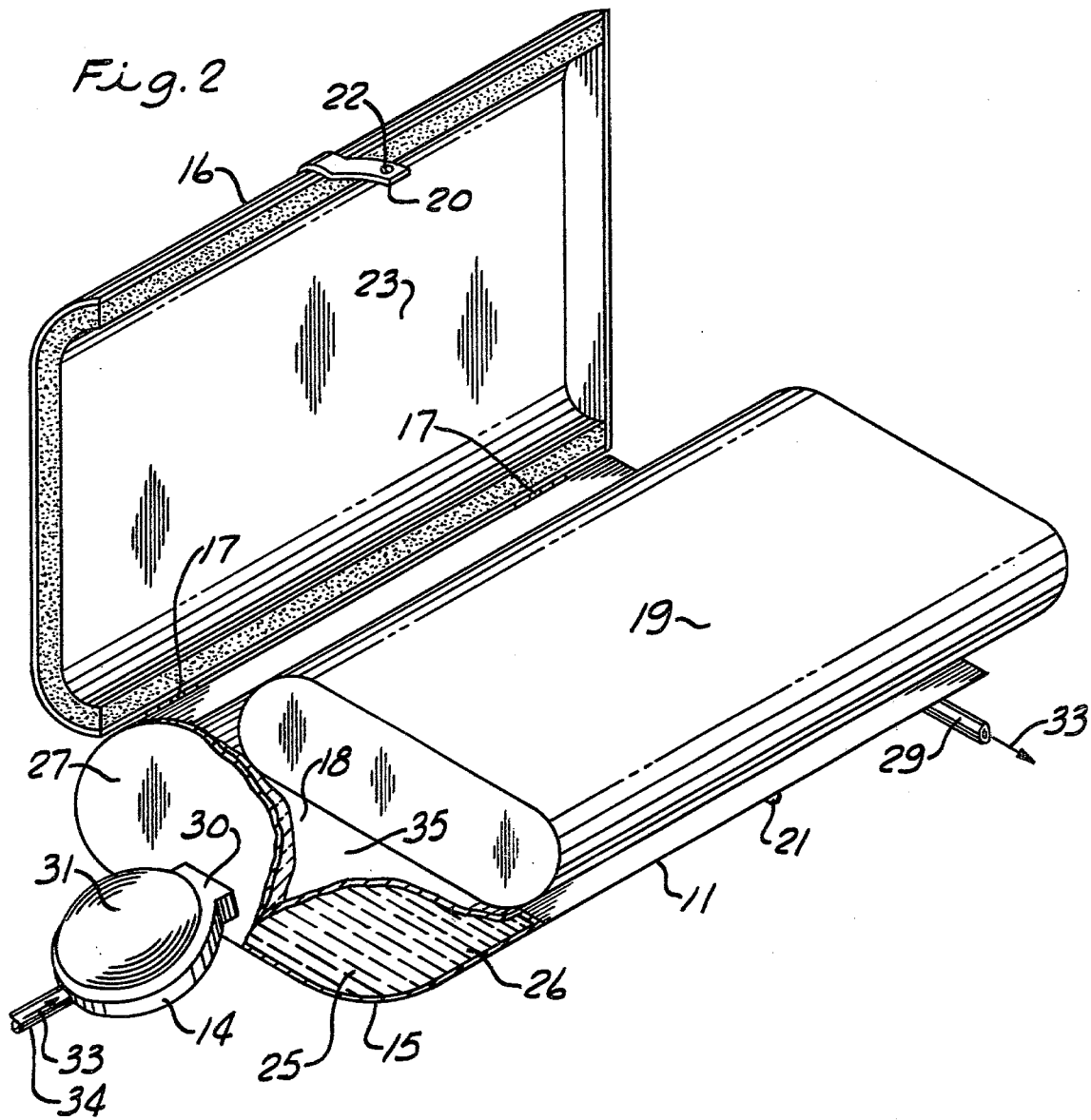

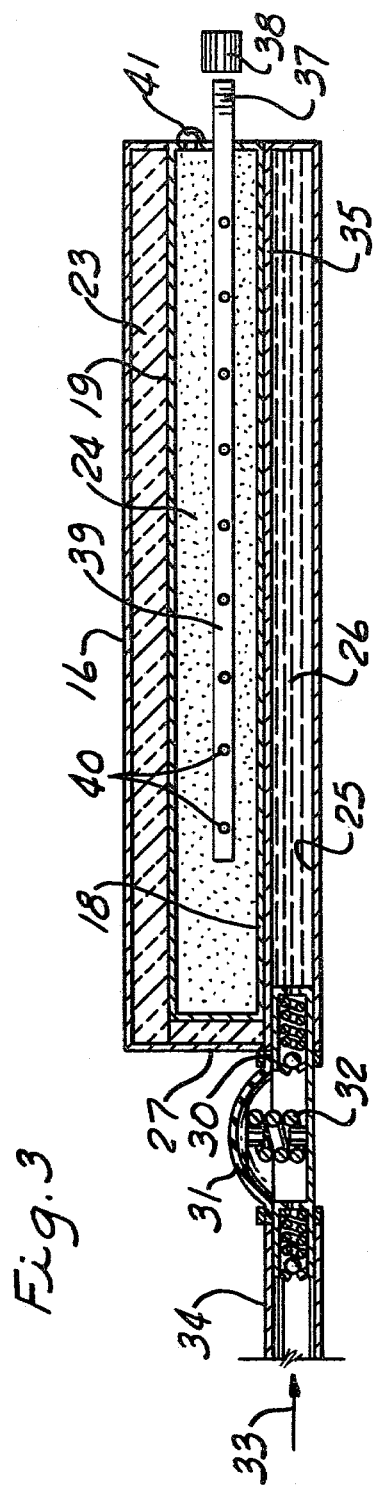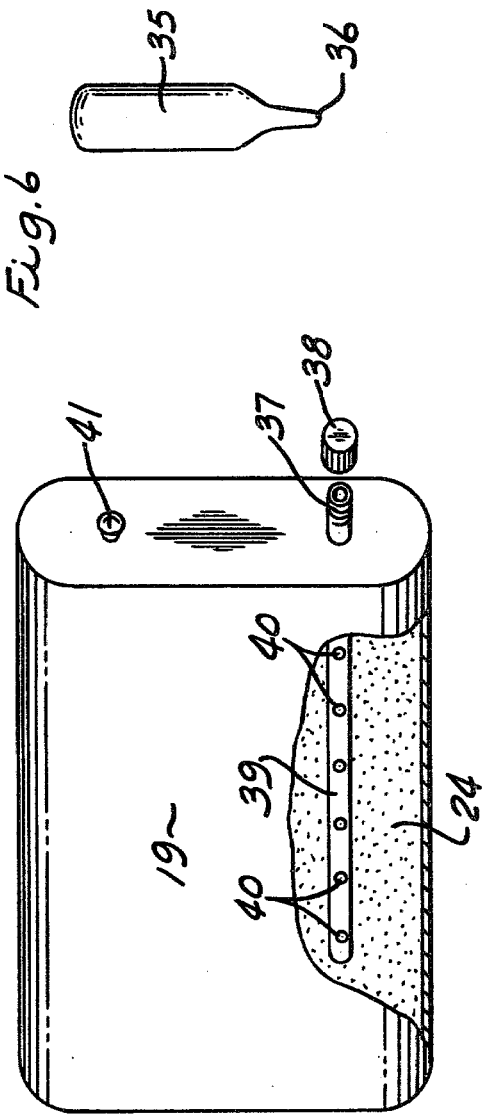

PORTABLE HEATER FOR GENERATING AND CIRCULATING HEAT IN WEARING APPAREL

CROSS REFERENCE TO RELATED APPLICATIONS

This application is a continuation-in-part of U.S. Application Ser. No. 049,059 filed June 18, 1979 now U.S. Pat. No. 4,281,418, which application is in turn a continuation-in-part of U.S. Application Ser. No. 875,815 filed Feb. 7, 1978, now U.S. Pat. No. 4,180,922 issued on Jan. 1, 1980.

BACKGROUND OF THE INVENTION

The present invention relates to portable furnaces and more particularly to compact furnaces or warmers to be carried on the person for circulating heat in wearing apparel such as gloves or boots.

Boot warmers wherein a hot liquid is circulated within a boot have been known in the past, for example, as illustrated in U.S. Pat. No. 518,579 issued to Annenberg et al and in U.S. Pat. No. 1,199,914 issued to Mossor. However, such boot warmers provide no compact means for heating the fluid and further require a rather awkward operation in getting the heated fluid into the boot cavities.

U.S. Pat. No. 912,527 issued to Batter on Feb. 16, 1909 discloses a portable boot and body warmer wherein a heater unit of relatively large size is attached to the individual's belt and fluid conduit tubes pass from the individual's belt down his legs and into his shoes or boots. Hand manipulated pumps are provided at the knee level to pump or circulate the fluid throughout the conduits. However, such an apparatus is extremely cumbersome and it is also relatively impractical in this day and age, and it is rather obvious that hunters and outdoor workers would not tolerate such a large amount of paraphernalia and tubes running down the legs and about the waist.

Liquid heater units for body warming purposes which are much more compact than that illustrated in Batter U.S. Pat. No. 912,527 have been developed as may be seen in U.S. Pat. No. 3,737,620. However, this compact heater unit, while being light weight and apparently very effective, is relatively complex and requires the use of nuclear fusion. The expense of such a device would clearly be beyond the reach of the average hunter or outdoor worker. In addition, this reference and the aforementioned reference do not teach how any of the devices disclosed could be more conveniently and economically and compactly utilized as a boot or glove warmer.

A major disadvantage of the economical heating units of the prior art which are utilized to circulate a heated liquid through wearing apparel is that these heating units must be used substantially in an upright position and will not effectively operate at any or all attitudes. In addition, the liquid furnaces of the prior art are, by necessity, too large in size and are cumbersome.

We have discovered that our boot warmer as disclosed in U.S. Pat. No. 4,180,922 is extremely effective. However, there are certain conditions under which this boot warmer cannot be utilized when solid fuel agglomerates are used in the furnace. For example, under some working conditions, as where explosive gases or dusts might be present, an open flame cannot be utilized. Also, in many working conditions, such as in the military and in many other outdoor occupations, there are times when an entire boot or glove or other wearing apparel may become completely submerged in water which would extinguish an ignited solid fuel agglomerate.

A principal object of the present invention is to eliminate these aforementioned disadvantages of the prior art and to provide a compact heating system for wearing apparel which is much more convenient and less expensive than the devices of the prior art.

SUMMARY OF THE INVENTION

The portable heater of the present invention for generating and circulating heat in wearing apparel such as gloves or boots or the like comprises a compact insulated case capable of being carried on one's person and having a cavity therein which is adapted to receive a chemical heat cartridge. The chemical heat cartridge is removably received in the cavity and the case is also provided with a liquid reservoir positioned for radiant heat transfer from the chemical heat cartridge through an inside heat exchange wall of the case. A flexible liquid conduit is provided which has both ends thereof connected for circulation of the heated liquid from said reservoir through the conduit in a closed circuit, and a pump is provided and connected to the conduit to circulate heated liquid from the reservoir through the conduit on demand.

The chemical heat cartridge consists of a sealed container which contains a chemical composition which reacts with an activating chemical when mixed therewith to provide an exothermic chemical reaction. An access is provided on the container with a closure which is replaceably removable to provide access to the interior of the container for the insertion of a predetermined quantity of activating chemical to initiate the exothermic reaction.

In one version of the chemical heat cartridge, a tube extends inside the container from the access and is provided with a series of apertures therein to assist in distribution of an activating chemical when inserted into the access in order to more uniformly distribute the catalyst or activating chemical with the chemical composition contained in the container. The cartridge may also be provided with a pressure release check valve to vent gas under pressure which may build up within the container as a result of the reaction of the activating chemical with the chemical composition contained within the container or heat cartridge.

BRIEF DESCRIPTION OF THE DRAWINGS

Other objects and advantages appear in the following description and claims.

The accompanying drawings show, for the purpose of exemplification without limiting the invention or the claims thereto, certain practical embodiments illustrating the principles of this invention wherein:

FIG. 1 is an isometric view in side elevation of the portable chemical heater of the present invention as utilized in a conventional boot.

FIG. 2 is an enlarged isometric view of the heater and pump unit of the present invention with the cover of the heater case opened to expose the chemical heat cartridge which is shown as being partially received within the cavity of the case, with portions further removed to expose the interior of the liquid reservoir.

FIG. 3 is a side view in mid cross-section of the heater unit illustrated in FIG. 2 with the cover closed and the chemical heat cartridge fully inserted within the cavity of the case.

FIG. 4 is an isometric view of the chemical heat cartridge contained within the heater illustrated in FIGS. 2 and 3, with portions thereof removed to expose the interior of the cartridge.

FIG. 5 is an isometric view of a felt boot liner in section with the portable chemical heater and pump assembly of the present invention installed on the top thereof.

FIG. 6 is a view in front elevation of a plastic capsule containing a predetermined quantity of an activating chemical or catalyst to be inserted in the chemical heat cartridge illustrated in FIG. 4 to initiate the exothermic chemical reaction therein.

DETAILED DESCRIPTION OF THE DRAWINGS

Referring to FIG. 1, the wearing apparel heater or warmer and boot combination 10 of the present invention includes a portable compact heater unit or heat exchanger 11 having a liquid conduit 12 circulating throughout and within boot 13 in order to circulate heated liquid from the heat exchanger unit 11. Heated liquid is pumped from unit 11 through conduit 12 by means of hand manipulated pump 14.

Referring particularly to FIGS. 2, 3 and 4, heater unit 11 is relatively compact and includes a compact case 15 having a cover 16 which is hinged at 17 to the remainder of case 15 and opens as indicated in FIG. 2 to provide cavity 18 therein to receive chemical heat cartridge 19 therein for giving off heat through a chemical exothermic reaction within cartridge 19. Cover 16 may be secured in its closed position by means of spring clip 20 which rides over and receives projection 21 within slot 22.

The bottom or back wall 35 of cavity 18 is a metal wall which is a good heat conductor and acts as an inside heat exchanger wall to transfer radiant heat from chemical heat cartridge 19 into the liquid 26 contained within the liquid reservoir 25 in order to heat the liquid 26. Case 15 is also insulated as indicated at 23 in order to prevent heat loss from cartridge 19 through the lid 16.

The entire case 15, with the exception of insulation 23 contained therein, is manufactured of a suitable metal such as chrome-plated steel. As best illustrated in FIG. 1, a filler spout 28 is provided at the top of the case 15 and provides access to liquid reservoir 25 for initially filling the reservoir with a suitable heat transfer liquid such as anti-freeze, or a combination of water and anti-freeze. Filler opening 28 is provided with a suitable plug.

Reservoir 25 is provided with an outlet 29 and an inlet 30. Hand pump 14 is secured to inlet tube 30, at the bottom of case 15, which communicates with the interior of reservoir 25. Hand pump 14 is a conventional double check valve pump having a flexible diaphragm 31 which is pumped or depressed by one's finger against the resistance of return coil spring 32 to pump liquid through pump 14 as indicated by arrows 33.

The inlet of pump 14 is indicated at 34 and conduit 12 is connected at one end to inlet 34 with a force fit and at the other end with a force fit over hot liquid discharge or outlet 29.

The entire heater unit 11 with pump 14 which is secured thereto are attached to the boot top as indicated in FIG. 4 by any conventional means such as a pocket or an adhesive. In FIG. 1, the entire unit is attached with an adhesive and the connection of conduit 12 to the unit also assists in holding it in position.

The chemical heat cartridge 19 is preferably made of a good heat conducting metal and is basically a sealed container containing a chemical composition 24 which reacts with an activating chemical when mixed therewith to provide an exothermic chemical reaction. There are many such chemicals on the market and by way of example, one may utilize the chemicals as disclosed in Rosmarin U.S. Pat. No. 2,675,798, Col. 3. Generally, this chemical 24 is activated by an activating chemical or catalyst such as water or alcohol or a combination thereof. Predetermined quantities of the activating chemical or catalyst are contained within the capsule illustrated in FIG. 6. Plastic capsule 35 has a nipple 36 at the bottom thereof which is cut with a scissors or the like so that the catalyst or chemical activator contained within capsule 35 may be squeezed out through the nipple 36 and thereby mixed with chemical 24 contained in chemical heat cartridge 19.

An access 37 is provided on cartridge or container 19 in order to insert the catalyst from capsule 35 into the interior of container 19 thereby mixing the catalyst with chemical composition 24 to create or initiate the exothermic reaction. Access 37 is provided with a replaceable removable closure or cap 38 which is threadably receivable on access 37.

A tube 39 extends inside container 19 from access 37 and is provided further with a series of apertures 40 to assist in distribution of the activating chemical when inserted into the access so that it is more uniformly mixed with the chemical composition 24 for reaction. Container 19 is further provided with a spring loaded pressure release check valve 41 in order to vent gas pressure built up within container 19 which may result from reaction of the activating chemical within capsule 35 with the chemical composition 24.

Check valve 41 is a standard and well known type which consists of a spring-loaded ball check valve.

In order to operate the portable heater of the present invention, anti-freeze or other suitable liquid is poured into the system of reservoir 25 and the conduit 12 by means of filler opening 28. While doing this, pump 14 is manipulated to fully circulate the liquid being poured into the system throughout the conduit and to purge air from the system back out through filler inlet 28. Once the system is filled, chemical cartridge 19 is inserted into cavity 18 with access 37 and vent 41 exposed at the top thereof and closure 38 is then removed and the activating chemical from capsule 35 is squeezed into access 37 and thereby thoroughly mixed with chemical composition 24 as the liquid activator penetrates through openings 40 of tube 39. Closure 38 is replaced over access 37 and the chemical action begins within container 19 in the form of an exothermic reaction thereby heating up container 19 which in turn heats heat exchanger wall 35 which in turn heats the liquid contained within reservoir 25. When the wearer then wants to heat his boots or gloves, as the case may be, he can manipulate pump 14 every 15 minutes to half-an-hour, or as desired, to circulate heated liquid in reservoir 25 through conduit 12 thereby warming the interior of the wearing apparel.

Capsule 35 as illustrated in FIG. 6 contains a predetermined quantity of the catalyst or activating chemical which is of an insufficient amount to completely react with all of the chemical 24 contained within container 19. Thus, the user may periodically reactivate the exothermic reaction within container 19 by adding new premeasured quantities of activating chemical to the interior of container 19 as required until the entire chemical composition 24 has been completely reacted with by the activating chemical. Once the chemical 24 within container 19 has been completely expended, the entire chemical heat cartridge 19 may then be discarded and a new cartridge inserted into unit 11.

The entire unit and combination boot and heater unit are very compact, and the portable heater of the present invention does not interfere with the normal activity of the boot wearer or glove wearer and requires no tubes or anything else attached elsewhere on the person of the wearer.

As illustrated in FIG. 5, the portable heater of the present invention may be provided in combination with a boot liner 40 with conduit 12' circulating throughout the boot liner 40. Felt boot liner 40 is of the conventional type which is inserted within a water-impervious boot casing such as illustrated at 13 in FIG. 1. Thus, the felt liner and portable heater combination may be sold as a separate unit and inserted into a wearer's existing boot casing.

The conduit 12' exits from the top of boot liner 40 so that the boot liner may be conveniently inserted within a boot casing and then the heater unit 11 hangs over top of the outside boot casing and may be secured thereto by a pocket on the outside of the boot casing or any other conventional securing means such as an adhesive or an expansion strap or belt strap. In either situation, the heater unit 11 is exposed such that pump 14 is exposed for easy access and manipulation as required.

In order to fill the system illustrated in FIG. 5 with the heat transfer liquid, one need only remove conduit 12' from heater outlet 29 or inlet 34 and fill the device through the opening, or a separate filler opening may be provided, as is the case with the unit illustrated in FIG. 1.

We claim:

1. A portable heater for generating and circulating heat in wearing apparel or the like comprising a compact case capable of being carried on a person and having a cavity therein adapted to receive a chemical heat cartridge, a chemical heat cartridge removably received in said cavity, a liquid reservoir in said case positioned for radiant heat transfer from said chemical heat cartridge through an inside heat exchanger wall of said case, a flexible liquid conduit having both ends thereof connected for circulation of the heated liquid from said reservoir through said conduit in a closed circuit, and pump means connected to said conduit to circulate heated liquid from said reservoir through said conduit on demand, said chemical heat cartridge consisting of a sealed container containing a chemical composition which reacts with an activating chemical when mixed therewith to provide an exothermic chemical reaction, and an access on said container and having a closure which is removable to provide access to the interior of said container for the insertion of an activating chemical.

2. The portable heater of claim 1 including a tube extending inside said container from said access and having apertures therein to assist in distribution of an activating chemical inserted into said access with said chemical composition for reaction.

3. The portable heater of claim 1 including a pressure relief check valve in said container to vent gas pressure buildup within said container resulting from reaction of said activating chemical with said chemical composition.

* * * * *